United States Patent
Brouwer-Brolsma et al.

(10) Patent No.: US 9,707,242 B2
(45) Date of Patent: Jul. 18, 2017

(54) USE OF 25-HYDROXYVITAMIN D3 TO ENHANCE EXECUTIVE FUNCTIONS

(71) Applicant: DSM IP ASSETS B.V., Heerlen (NL)

(72) Inventors: Elske Maria Brouwer-Brolsma, Kaiseraugst (CH); Edith Johanna Maria Feskens, Kaiseraugst (CH); Lisette De Groot, Kaiseraugst (CH); Stephanie J. M. Krammer-Lukas, Kaiseraugst (CH); Hasan Mohajeri, Kaiseraugst (CH); Szabolcs Peter, Kaiseraugst (CH); Jonas Witter-Schegg, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/780,299

(22) PCT Filed: Mar. 27, 2014

(86) PCT No.: PCT/IB2014/060214
§ 371 (c)(1),
(2) Date: Sep. 25, 2015

(87) PCT Pub. No.: WO2014/155332
PCT Pub. Date: Oct. 2, 2014

(65) Prior Publication Data
US 2016/0038513 A1 Feb. 11, 2016

(30) Foreign Application Priority Data

Mar. 27, 2013 (EP) .................................... 13161242

(51) Int. Cl.
*A61K 31/593* (2006.01)
*A61K 9/00* (2006.01)
*A23L 33/155* (2016.01)

(52) U.S. Cl.
CPC .......... *A61K 31/593* (2013.01); *A23L 33/155* (2016.08); *A61K 9/0053* (2013.01); *A23V 2002/00* (2013.01)

(58) Field of Classification Search
None
See application file for complete search history.

(56) References Cited

U.S. PATENT DOCUMENTS

2013/0034530 A1   2/2013   Fantz

FOREIGN PATENT DOCUMENTS

| WO | WO 95/02409 | 1/1995 |
| WO | WO 2009/101132 | 8/2009 |
| WO | WO 2013/040419 | 3/2013 |

OTHER PUBLICATIONS

International Search Report for PCT/IB2014/060214, mailed Jun. 3, 2014, 5 pages.
Kjaergaard et al., "Effect of vitamin D supplement on depression scores in people with low levels of serum 25-hydroxyvitamin D: nested case-control study and randomised clinical trial", British Journal of Psychiatry, vol. 201, No. 5, Nov. 1, 2012, pp. 360-368.
Lee et al., "Association between 25-hydroxyvitamin D levels and cognitive performance in middle-aged and older European men", Journal of Neurology Neurosurgery & Psychiatry, vol. 80, No. 7, Jul. 1, 2009, pp. 722-729.
Buell et al., "Vitamin D is associated with cognitive function in elders receiving home health services", Journals of Gerontology, Series A, Biological Sciences and Medical Sciences, vol. 64, No. 8, Aug. 1, 2009, pp. 888-895.
Dean et al., "Effects of Vitamin D supplementation on cognitive and emotional functioning in young adults—A randomised controlled trial", PLOS ONE, vol. 6, No. 11, Nov. 2011.
Oudshoorn et al; *Higher Serum Vitamin $D_3$ Levels are Associated with Better Cognitive Test Performance in Patients with Alzheimer's Disease;* Dement Geriatr Cogn Disord 2008; 25:539-543.
Official Action, CN Appln. No. 2014-80018584.3, Jul. 1, 2016.

*Primary Examiner* — Brian J Davis
(74) *Attorney, Agent, or Firm* — Nixon & Vanderhye P.C.

(57) ABSTRACT

This invention relates to the use of 25-hydroxyvitamin D3 (25-OH D3) to increase or maintain or alternatively, to lessen the decrease of the cognitive element known as executive functioning in healthy individuals. Optionally, 25-OH D3 may be administered in combination with Vitamin D or other ingredients.

5 Claims, No Drawings

USE OF 25-HYDROXYVITAMIN D3 TO ENHANCE EXECUTIVE FUNCTIONS

This application is the U.S. national phase of International Application No. PCT/IB2014/060214 filed 27 Mar. 2014, which designated the U.S. and claims priority to EP Patent Application No. 13161242.6 filed 27 Mar. 2013, the entire contents of each of which are hereby incorporated by reference.

BRIEF DESCRIPTION OF THE INVENTION

This invention relates to the use of 25-hydroxyvitamin D ("25-OH D3"), either alone or in combination with Vitamin D3 to enhance and/or maintain certain aspects of cognition in humans, particularly in the area of executive functioning.

BACKGROUND OF THE INVENTION

Aging has been shown to be one of the risk factors for the development of vitamin D deficiency. It is also generally known that ageing is a key risk factor for cognitive decline and dementia. Mice lacking vitamin D receptors (VDRs) demonstrate an increased anxiety level, inferior nest building, and impaired motor performance, which suggests a role for vitamin D in various brain processes. Mechanistically, there appears to be an effect of vitamin D on intraneuronal calcium regulation and the synthesis and degradation of several neurotransmitters and neurotrophins. Further, Vitamin D has been suggested to beneficially affect amyloid 13 phagocytosis and clearance by macrophages Although a recent review by Eyles et al. 2012 *Front. Neuroendocrinol.* (http://dx.doi.org/10.1016/j.yfrne.2012.07.001) showed that a role for vitamin D in certain brain functions is confirmed by neurobiological evidence, they also concluded that there is still insufficient and inconsistent data from epidemiological studies and well-designed randomized controlled trials in humans to verify this.

Several human population based studies investigated the possible role of 25-OH D3 in cognitive performance, although none of these describe intervention trials involving 25-OH D3:

Annweiler et al 2009 *Eur J Neurol* 16(10):1083-1089 looked at the literature for studies showing a significant positive correlation between 25-OH D3 levels and cognitive performance. The results were inconsistent.

Breitling et al 2012 *Experimental Gerontology* 47(1):122-127 found that low vitamin D levels are associated with worse cognitive function in the elderly assessed after 5 years. High levels of vitamin D showed a plateau of cognitive performance functioning.

Data from Brouwer-Brolsma et al 23 Jun. 3, 2012 *Eur J. Nutr.* online publication DOI 10.1007/s00394-012-0399-0 did not support the hypothesis that higher 25-OH D3 levels were associated with better cognitive functioning. There was no information reported specifically on executive functioning.

Chan et al. *J Affect Disord.* April 2011; 130(1-2):251-259. Serum levels of 25-OH D3 were found to be inversely associated with depression. However, no association was found between 25-OH D3 levels and cognitive impairment. Specific effects on executive functioning were not reported.

Seamans et al 2010 *Eur. J Clin Nutr.* 4(10):1172-1178 looked at associations between serum 25-OH D3 status and various aspects of cognitive function. There was an association between 25-OH D3 levels in some aspects of spatial working memory, but not all such aspects.

Lee et al 2009. *J Neurol Neurosurg Psychiatry* 80(7):722-729 found that lower scores on the Digital Symbol Substitution Test were associated with lower 25 OH D3 levels, but this correlation was not seen for other cognitive tests.

WO 1995/02409 (Trustees of the Univ of Kentucky) disclose use of vitamin D, its metabolites and precursors to protect against neuron loss, such as is observed in Alzheimers and other neuronal based diseases.

It would be desirable to provide a safe, effective way to enhance or retain cognitive executive functioning in healthy people.

DETAILED DESCRIPTION OF THE INVENTION

It has been found, in accordance with this invention that serum 25-hydroxyvitamin D3 (25-OH D3) levels are positively associated with the cognitive processes referred to as "executive function" and thus can be used to maintain or enhance executive functioning, or to lessen the decrease of cognitive function in healthy individuals. However, it has also been found, in accordance with this invention, that there is not always a significant correlation between vitamin D intake and serum 25-OH D3 levels, particularly in elderly people; and it is presumed sunlight exposure may be more influential.

Thus one aspect of this invention is the administration of 25-OH D3 to maintain or enhance executive functioning in healthy individuals. Another aspect of this invention is the non-therapeutic use of 25-OH D3 for enhancing or maintaining cognitive executive function. Another aspect of this invention is the use of 25-OH D3 in the manufacture of a pharmaceutical, food, or nutraceutical product to enhance or maintain cognitive executive function.

Another aspect of this invention is directed to a method of enhancing, maintaining, or decreasing a lessening of cognitive executive function performance comprising:
 administering to a healthy human desirous of enhancing or maintaining cognitive-executive-function an effective amount of 25-hydroxyvitamin D3.

Another aspect of this invention is directed to a method of enhancing, maintaining, or lessening a decrease of cognitive executive function performance comprising:
 orally administering to a healthy human desirous of enhancing or maintaining cognitive-executive-function an effective amount of 25-hydroxyvitamin D3 prior to an executive function assessment,
 challenging the healthy human with a task requiring executive functioning, and assessing the individual's resulting enhanced or maintained executive function.

This invention also relates to a kit for maintaining, enhancing, or lessening the decrease of executive function comprising:
 a) an oral dosage form of 25-OH D3; and
 b) information which informs a prospective user about the benefits of using 25-OH D3 in enhancing, maintaining, or lessening the decrease of cognitive executive function in healthy individuals.

A further aspect of this invention is the prevention of executive dysfunction, lessening the severity of executive dysfunction, and/or delaying the onset of executive dysfunction in a healthy individual through the use of orally administered 25-OH D3. These uses also include the non-therapeutic uses.

The enhancing or maintaining of cognitive executive function by use of orally administered 25-OH D3 may optionally further comprise the use, including the non-therapeutic use of Vitamin D in combination with the 25-OH D3.

Another aspect of this invention is the non-therapeutic use of 25-OH D3 in people who are vitamin D deficient, in order to positively affect an aspect of executive functioning.

Another aspect of this invention is the use of 25-OH D3 and optionally Vitamin D3 as the sole active ingredient which has executive-function-enhancing properties in admixture with further active ingredients. The further ingredients may benefit other aspects of health, and may be other vitamins, minerals, sources of calories, plant extracts, or other such medicinal or active ingredients. However, the further ingredients do not affect executive functioning.

DEFINITIONS

As used throughout the specification and claims, the following definitions apply:

Executive function—this is an umbrella term for cognitive processes that regulate, control and manage other cognitive processes, including such aspects as: planning, working memory, attention, problem solving, verbal reasoning, inhibition, mental flexibility, task switching, semantic memory, verbal fluency, and initiation and monitoring of actions. The prefrontal areas of the frontal lobe are necessary but not sufficient for carrying out these functions.

Executive system—is a theorized cognitive system in psychology that controls and manages other cognitive processes. It is responsible for processes that are sometimes referred to as executive functions, executive skills, supervisory attentional system, or cognitive control. The prefrontal areas of the frontal lobe are necessary but not sufficient for carrying out these functions.

Healthy individual—when used in context of this invention, the healthy individual does not have any of the following conditions: depression, Alzheimer's Disease, schizophrenia, autism, Parkinson's disease, psychotic conditions (such as sub clinical schizophrenia), Alzheimer's-like dementia, AIDS-dementia complex, other dementias, glucose intolerance, diabetes, or conditions requiring kidney or liver transplants. Further, a "healthy individual" has not previously received 25-OH D3 for the treatment of osteoporosis, or physical conditions related to Vitamin D deficiency.

"Vitamin D" means either Vitamin D3 (cholecalciferol) and/or Vitamin D2 (ergocalciferol). Humans are unable to make Vitamin D2 (ergocalciferol), but are able to use it as a source of Vitamin D. Vitamin D2 can be synthesized by various plants and is often used in Vitamin D supplements as an equivalent to Vitamin D3.

"Prevent" is meant to include amelioration of the disease, lessening of the severity of the symptoms, early intervention, and lengthening the duration of onset of the disease, and not intended to be limited to a situation where the patient is unable to experience any symptoms of executive function impairment.

"Vitamin D deficient" means that the serum levels of 25-OH D3 are between 25 to 49 nmol/l. Amounts less than 25 nmol/l are considered severely deficient.

"Vitamin D sufficient" means that the serum levels of 25-OH D3 are between 50 to 75 nmol/l; levels above 75 nmol/l are generally considered desired or optimal.

This invention is also concerned with the use of 25-OH D3, and optionally together with Vitamin D3 for the use of increasing, maintaining, or lessening the decrease of executive function in an individual who does not have any of the following conditions: depression, Alzheimer's Disease, schizophrenia, autism, Parkinson's disease, psychotic conditions (such as sub clinical schizophrenia), Alzheimer's-like dementia, AIDS-dementia complex, other dementias, glucose intolerance or diabetes.

The 25-OH D3 may be administered to a person who has less than normal serum levels of 25-OH D3 or, alternatively to someone whose blood serum levels are normal. One of the aspects of this invention is that administration of 25-OH D3 (as opposed to D3) can result in an increase of serum 25-OH D3 levels and that this can lead to a clinically significant increase in executive functioning. In some embodiments, particularly where the individual has less than normal serum levels of 25-OH D3, the individual may be given the combination of 25-OH D3 and Vitamin D3.

This invention is also drawn to a human pharmaceutical or nutraceutical or food supplement composition wherein the active ingredients consist essentially of a combination of Vitamin D and 25-OH D3; and more preferably, the active ingredients consist essentially of a combination of Vitamin D3 and 25-OH D3 which is useful for increasing or maintaining executive functioning.

In another embodiment, a kit is provided which is comprised of multiple, separate dosages of Vitamin D or Vitamin D3 along with a dosage of 25-OH D3. They may be enclosed in a container: e.g., bottle, blister pack, or vial rack. Further, instructions for administering the composition as a dosage to a human are provided within the kit.

The peak concentration of 25-OH D3 achieved by such administration may be from 30 nmol/L to 375 nmol/L, preferably from about 120 nmol/L to about 300 nmol/L. The steady-state concentration of 25-OH D3 achieved by such administration is preferably from above 60 nmol/L.

The prefrontal cortex seems to be an area of the brain which is a key determinant of executive function, although other areas of the brain may also be involved. Thus, another aspect of this invention is the use of 25-OH D3 as a pre-frontal cortex protectorant.

Examples of abilities which involves Executive Functions include:

Planning: foresight in devising multi-step strategies.
Idea generation & concept finding: the ability to build ideas based on prior knowledge
Flexibility: capacity for quickly switching to the appropriate mental mode.
Inhibition: the ability to withstand distraction, and internal urges.
Anticipation: prediction based on pattern recognition.
Critical evaluation: logical analysis.
Working memory: capacity to hold and manipulate information "on-line" in our minds in real time.
Fuzzy logic: capacity to choose with incomplete information.
Divided attention: ability to pay attention to more than one thing at a time.
Decision-making: both quality and speed People who would potentially benefit from enhancing executive function or maintaining healthy executive function would include the following categories:

a) People with learning disabilities (ID) and attention-deficit hyperactivity disorder—(ADHD). Both LD and ADHD have been associated with executive dysfunction. Therefore otherwise healthy people who are experiencing ADHD or LD can benefit from oral administration of 25-OH D3.

b) Academic skills—executive function is involved in academic skills such as reading comprehension, writing essays or writing projects, and taking tests. Increasing executive function according to this invention would be useful for students, people learning new subjects, people who need to organize information for their jobs, people who write reports, and people who need to take examinations.

c) Long term projects—executive function is involved in long term planning and completing complex tasks. For example, the ability to time manage, set realistic milestones, monitoring progress during a project, and organizing projects are all liked to executive function. Thus, people who are involved in managing projects would benefit from this invention.

d) Shifting between tasks—the ability to "multitask", i.e. being able to shift rapidly between two or more tasks without becoming confused is also a type of executive function. Thus people who are expected to multitask could benefit from 25-OH D3.

e) Idea generation—the ability to function creatively, such as a writer, editor, inventor, scientists, and others.

Another aspect of this invention is that orally administered 25-OH D3, either alone or in combination with Vitamin D3 can increase serum plasma levels, and thus maintain, enhance and/or prevent the lessening of executive function. The combination of both active ingredients may be particularly advantageous as it 1) results in a rapid and synergistic plasma response of 25-OH D3; and 2) leads to an pronounced and long plateau of plasma 25-OH D3 levels.

Thus, this invention would be of particular interest to the following healthy people who are desirous in preserving, enhancing, or maintaining their executive functioning: aging people, students, researchers, academics, writers, editors, lawyers, politicians, artists, performing artists (including those in theatre, opera, radio, television, cinema or circus), choreographers, directors, those facing a test or examination, those who organize events, tasks, and or processes, such as project planners, military commanders, other type of coordinators, people expected to carry out multitasking, such as air traffic controllers, pilots, teachers, service personnel, medical personnel, and/or managers.

Formulations

The nutraceutical and pharmaceutical compositions according to the present invention may be in any galenic form that is suitable for administering to humans, but oral forms are preferred, e.g. in solid form, such as additives/supplements for food, food, fortified food or feed, tablets, pills, granules, dragées, capsules, gummy formulations, and effervescent formulations such as powders and tablets, or in liquid form such as solutions, emulsions or suspensions as e.g. beverages, pastes and oily suspensions. The pastes may be encapsulated in hard or soft shell capsules, whereby the capsules feature e.g. a matrix of (fish, swine, poultry, cow) gelatin, plant proteins or lignin sulfonate. The dietary and pharmaceutical compositions may be in the form of controlled (delayed) release formulations.

The dietary compositions according to the present invention may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents, gel forming agents, antioxidants and antimicrobials.

In addition the pharmaceutical or nutraceutical compositions according to the present invention may further contain conventional pharmaceutical additives and adjuvants, excipients or diluents, including, but not limited to, water, gelatin of any origin, vegetable gums, lignin sulfonate, talc, sugars, starch, gum arabic, vegetable oils, polyalkylene glycols, flavoring agents, preservatives, stabilizers, emulsifying agents, buffers, lubricants, colorants, wetting agents, fillers, and the like. The carrier material can be organic or inorganic inert carrier material suitable for oral/parenteral/injectable administration.

Examples of food which may be supplemented or fortified with 25-OH D3 or optionally both 25-OH D3 and vitamin D include cereal bars, dairy products, such as yoghurts, and bakery products, such as breads, cakes and cookies, non-alcoholic drinks, such as soft drinks, fruit juices, lemonades, near-water drinks, teas and milk-based drinks, in the form of liquid food, such as soups and dairy products (muesli drinks).

Dosages

The combination of vitamin D and 25-OH D3 may be administered once per day, once per week, or once per month. Delivering a combination of the Vitamin D and 25-OH D3, results in plasma levels of 25-OH D3 increase synergistically. This effect is observed rapidly, and is most pronounced after about the first 6 hours. Further, the increase in plasma levels is sustained (albeit at a lower, but still clinically effective level), for at least approximately 206 hours. The rapid effect provides acute bioavailability, while the sustained elevated plasma levels ensures extended bioavailability.

Daily.

A composition according to this invention where the two active ingredients are to be administered in separate dosage forms, contains Vitamin D or 25-OH D3 in an amount from about 1 µg to about 50 µg, preferably about 5 µg and 25 µg. Alternatively, a single daily dosage having both Vitamin D and 25-OH D3 contains each active ingredient in an amount from about 1 µg to about 50 µg, preferably about 5 µg and 25 µg. Where 25-OH D3 is the only active ingredient with Vitamin D-type activity, then its dosage is about 1 µg to about 50 µg.

The dosage ratio of Vitamin D to 25-OH D3 may be from about 50:1 to about 1:50, more preferably from about 25:1 to about 1:25, and even more preferably from about 6:1 to about 1:6.

Multiple, separate dosages may be packaged in a single kit (or container). For example, the kit may be comprised of thirty separate daily dosages of both actives separately (i.e. 60 separate dosages), or combined (i.e. 30 dosages containing both active ingredients). Instructions for administering the dosages to a human may be included in the kit.

Weekly.

A single weekly dosage contains 25-OH D3 in an amount from about 7 µg to about 350 µg, and preferably from about 35 to 175 µg. Alternatively, a single weekly dosage may contain both Vitamin D and 25-OH D3 each in an amount from about 7 µg to about 350 µg, and preferably from about 35 to 175 µg. The dosage ratio of Vitamin D to 25-OH D3 may be from about 50:1 to about 1:50, more preferably from about 25:1 to about 1:25, and even more preferably from about 6:1 to about 1:6.

Monthly.

A single monthly dosage contains Vitamin D or 25-OH D3 in an amount from 30 µg to about 1500 µg, preferably about 75 µg to about 500 µg. Alternatively, a single monthly dosage may contain both Vitamin D and 25-OH D3 each in an amount from 30 µg to about 1500 µg, preferably about 75

µg to about 500 µg. A kit may be comprised of one, two, three, four, five, six, seven, eight, nine, ten, eleven, or twelve weekly or monthly dosages.

Dosage ratios of Vitamin D to 25-OH D3 should range between 50:1 to about 1:50, more preferably from about 25:1 to about 1:25, and even more preferably from about 6:1 to about 1:6. It has been found that a dosage ratio of approximately 6:1 Vitamin D to 25-OH D3 is particularly beneficial in increasing plasma 25-OH D3 levels quickly (i.e. within a few hours) and maintaining elevated plateau levels.

Executive Functioning Illustrated

Simply put, a question about executive function asks "how" or "whether" a person will do something (e.g. Will you do Activity X? If so, how and when?). In contrast, questions about cognitive functions are generally phrased in terms of "what" or "how much" (e.g. What do you know? What can you do?). To further illustrate, suppose a person decides they want to learn a new subject such as a foreign language. Executive functions are involved in the decision to try something new, planning for learning, i.e. finding a class or tutor, finding instructive books, re-arranging one's schedule to permit time to study, and the decision to concentrate on the study materials.

A person experiencing a problem with executive function may experience difficulties as described below:

1. Difficulty to decide and coordinate the correct order of steps to perform an action, such as walking, speaking, lifting up an object and putting it down where it belongs, or operating a phone.
2. Difficulty starting, continuing, shifting, or stopping an action including several steps such as driving from A to B.
3. Difficulty holding pieces of information in memory storage to guide choices, thus forgetting key pieces of information and making wrong choices. For example, forgetting an announcement about a friend not coming to an event may lead to asking why that person has not come yet.
4. Difficulty identifying appropriate responses and honoring limits, for example knowing when to add comments to a discussion, not touching or speaking to strangers, or not handling an art object (next to a "Do Not Touch" sign) at a store or museum.
5. Difficulty holding back spontaneous actions or comments though they may be rude, hurtful, untimely, or against rules or the law. The person may be surprised when a spontaneous action such as driving the car through a stop sign or red light, results in hitting another car. The unsafe driver with executive function decline may accuse the other (not-at-fault) driver, "You should have gotten out of the way."
6. Difficulty keeping emotions stable, in other words having sudden outbursts of anger, acting irritated or rude, or laughing when others are serious or grieving the loss of a loved one. The emotion may be extreme or not fit the situation or the interactions of others. The emotions may appear disconnected from genuine concern (in other words the person may appear indifferent to the emotion which others express).
7. Difficulty keeping up with the pace of activity or conversation. Acting very slow when thinking, moving, and talking, as if one had "jet lag" or was in a slow motion movie.
8. Difficulty thinking about consequences before acting though still highly intelligent. Unable to apply past consequences to current choices or actions. For example, the person may spontaneously buy several magazines that are never read or buy (through the mail or at stores) several products that are never used.
9. Difficulty shifting from one set of ideas, a phrase, or actions to the next step or to a different idea or activity. Acting as if stuck in a rut for a period of time.
10. Difficulty planning new actions when there is an unexpected change, for example seeing that a street and sidewalk are closed for repair and walking there anyway.

So long as executive functions are intact, a person can sustain considerable cognitive loss and still continue to live independently, constructively self-serving, and productive. Loss of executive functions means that the person may no longer be capable of satisfactory self-care, holding a job, or maintaining normal social relationships, regardless of how well preserved the person's cognitive capabilities are (i.e. the person can still score high on tests of skills, knowledge and abilities).

Cognitive deficits usually involve specific functions or functional areas whereas executive functions tend to be global, affecting all aspects of behavior. Executive functions can affect cognitive function in that the person has impaired ability in approaching and/or motivation to take the decision for planning or carrying out a cognitive task, or in the monitoring of performance.

Differentiated from Alzheimer's Disease or Other Dementias

It is noted that there are reports that vitamin D may have some benefit in patients suffering from Alzheimer's Disease ("AD") or other dementias. This invention is to be differentiated from these observations, in that a) the population of persons receiving the 25-OH D3 and optionally D3 in accordance with this invention is a healthy population, and b) the effect in the AD population seems to be related to the vascular pathway, whereas in this invention, while not wishing to be bound by theory, it appears that a different mechanism is at work.

In vascular dementia, there are mainly subcortical deficits/features, but there is mostly focal cortical damage. An MRI shows diffuse and often confluent white matter pathology involving the periventricular zone and deep white matter (leucoaryosis) as a consequence of deep penetrating blood vessels. In contrast to AD the episodic memory deficit is less dense and involves recall more than retrieval. Patients show deficits on executive tasks requiring mental flexibility, shifting and response inhibition.

In the beginning of AD mainly memory and language are affected. Attention and executive functioning are in the beginning of AD often still unaffected.

In AD or cortical dementia, the grey matter, which affecting predominantly memory, language and visuo-spatial abilities is damaged. Epic memory (such as recall, recognition severely affected) is often one of the first signs. Attention and executive functions are in the first stage quite well preserved. An MRI often shows hippocampal atrophy—early stage only detected when volumetric analyses are conducted. Functional scans may show changes with posterior cingulate and/or bilateral parieto-temporal hypometabolism.

Another aspect of this invention is the use of 25-OH D3 and optionally Vitamin D to improve one of the aspect of executive functions selected from the group consisting of:

a) Concept shifting interference; (this is the executive function which is measured by e.g., the TMT B test);

b) Susceptibility to behavioral interference (this is the executive function which is measured e.g., by the Stroop test);
c) Fluency or semantic memory (this is the executive function which is measured e.g., by the "animal naming" test)
d) Reaction time response to visual stimuli measured by e.g., the Reaction Time test.

The following non-limiting Examples are presented to better illustrate the invention.

EXAMPLE 1

25-OH D3 Levels and Executive Function

Analyses were performed using baseline data of 127 participants of the ProMuscle study, which was originally designed to study the effect of protein supplementation, in combination with or without progressive exercise training on muscle function and muscle mass. Eligibility was defined as being 65 years or older and being frail or pre-frail. Frailty was defined according to the criteria from Fried et al. as having unintentional weight loss, weakness, self-reported exhaustion, slow walking speed, and/or low physical activity. A participant was classified as pre-frail when one or two of the aforementioned criteria were met, while frail was classified when three or more criteria were present. Participants were excluded if they had fasting plasma glucose (FPG) levels=7.0 mmol/L, cancer, Chronic Obstructive Pulmonary Disease, renal failure or when they participated in any structured exercise training program in the past two years. The Wageningen University Medical Ethical Committee approved the study and all participants gave their written informed consent.

Mental Well-being

Overall cognitive functioning was assessed using the Mini Mental State Examination (MMSE). The variable for analyses was defined as the maximum MMSE score minus the MMSE score of the participant, reflecting the number of erroneous answers. Domain-specific cognitive performance was measured using an extensive cognitive test battery, performed by well-trained research assistants and according to a strict protocol. The cognitive test battery included the Word Learning Test (WLT) direct recall, decayed recall and recognition to measure episodic memory; Wechsler digit span forward and backward test to determine attention and working memory; Trail Making Test-A (TMT-A and Trail Making Test-B (TMT-B) to assess information processing speed and concept shifting interference; Stroop Color-Word Test to determine selective attention and susceptibility to behavioral interference; and the Verbal fluency test and Reaction Time Task to measure executive functioning. Apart from the Reaction Time Task, all aforementioned tests were always performed in the afternoon. Reaction time (RT) was assessed during the morning, in fasted state, by the computerized finger pre-cueing task.

Biochemical Analyses

Blood samples were collected at baseline while participants were in a fasting state. EDTA containing tubes were centrifuged at 1000×g at 4° C. for 10 min and serum tubes were centrifuged 90 min after the blood collection at 1000×g at 18° C. for 30 min. Aliquots of plasma and serum were frozen in liquid nitrogen and stored at −80° C. until further analysis. Plasma glucose concentrations were analyzed with a COBAS FARA analyzer (Uni Kit III; Roche, Basel, Switzerland). Insulin was analyzed by radioimmunoassay (Insulin RIA Kit; LINCO Research Inc, St Charles, Mo.). Serum 25-OH D3 was measured by isotope dilution—online solid phase extraction liquid chromatography—tandem mass spectrometry (ID-XLC-MS/MS)—which was performed at the Endocrine Laboratory of the VU University Medical Center. Serum 25-OH D3 was released from its binding protein(s) and a deuterated internal standard (IS: 25-OH D33-d6) was added. Samples were extracted and analysed by XLC-MS/MS (a Symbiosis online SPE system (Spark Holland, Emmen, the Netherlands) coupled to aQuattro Premier XE tandem mass spectrometer (Waters Corp., Milford, Mass.)). Method characteristics: LOQ 4.0 nmol/L; intra-assay CV<6% and inter-assay CV<8% for 3 concentrations between 25 and 180 nmol/L.

Dietary Intake

Dietary intake data were obtained by 3-day food records. Trained dieticians gave oral and written instructions about recording the type of foods and estimation of portion sizes in household measures. At a second visit, dieticians checked the food records for completeness, obtained additional information about unclear items or amounts, and used examples household measures to improve the estimation of portion sizes. The days of recording were randomly assigned so that all days of the week, including weekend days, were equally represented. Dietary intake data were coded (type of food, time of intake, and amount) and energy and macronutrient intakes were calculated using a nutrient calculation program (BAS nutrition software, 2004, Arnhem, the Netherlands) and the Dutch food composition database.

Covariates

Height was measured at baseline with a wall-mounted stadiometer to the nearest 0.1 cm. Weight was measured in a fasted state to the nearest 0.1 kg with a calibrated digital scale (ED-6-T; Berkel, Rotterdam, The Netherlands). Subsequently, Body Mass Index (BMI) was calculated as weight/height$^2$. Information on education level (primary, secondary or higher education), smoking status (non-smoker or current smoker), medical history and presence of chronic disease (including kidney disease, liver disease, cardiovascular disease, muscle disease, hip- or knee replacement) was collected using questionnaires. Blood pressure was measured in the morning after 10 minutes of rest in supine position with an Omron HEM-907 (Lake Forest, Ill., USA) device. Habitual physical activity was quantified using a triaxial accelerometer (ActiGraph GTX3, 2009, Pensacola, Fla.) worn on the hip for 1 week. Change of acceleration per second and epochs of 60 seconds were used. After 7 days, data were uploaded for analysis and analyzed using the MAH/UFFE analyzer, version 1.9.0.3 (MRC 149 Epidemiology Unit, Cambridge, UK). Data files that did not meet 10 hours of monitoring per day on at least 5 days as well as files that included periods of >100 min without activity were excluded from the analysis.

Statistical Analyses

Characteristics of the study population are reported using the mean with standard deviation (SD), or as percentages. Medians with interquartile range were used to report skewed variables. Chi-squared tests for categorical variables and 1-way analysis of variance for continuous variables were performed to compare baseline characteristics over tertiles of 25-OH D3. Multivariable regression analyses were performed to study the associations of 25-OH D3 with domain-specific cognitive functioning. To compare the results of the individual cognitive tests and to limit the number of dependent variables, crude test scores were clustered into compound Z-scores for four neuropsychological domains: Episodic memory, Attention and working memory, Information processing speed, and Executive functioning. In formula form:

Episodic memory=(WLT total immediate recall+ WLT decayed recall+WLT recognition)/3;

attention and working memory=(Digit Span forward+Digit Span backward)/2;

information processing speed=(Average Stroop card 1 and 2+−TMT-A+−RT uncued)/3;

Executive Functioning=(Stroop ratio+Verbal Fluency+−TMT−ratio+−RT finger-cued+−RT hand-cued+−RT neither-cued)/6.

WLT decayed recall was calculated as the number of words recalled after approximately 15 minutes following the fifth session of the WLT minus the number of words recalled during the fifth session of the WLT.

Stroop ratio was calculated by: Stroop card 3/((Stroop card 1+Stroop card 2)/2).

Accuracy and speed-accuracy trade-off (SATO) were calculated to take into account errors made during the Stroop Test. Accuracy=(maximum right answers—amount of errors/maximum right answers). SATO=accuracy/time needed to complete the task. T MT-ratio was calculated by TMT-B/TMT-A.

As MMSE-score followed a Poisson distribution, Rate Ratios (RRs) for 25-OH D3 and global cognitive performance were calculated using multivariable Poisson regression with the number of erroneous answers as outcome for global cognitive functioning. This RR corresponds to the probability of developing depression or global cognitive dysfunction in participants with either intermediate or highest 25-OH D3 levels in this population compared to participants with the lowest 25-OH D levels.

Participants were categorized according to tertiles of 25-OH D3, using the lowest tertile as the reference category. All analyses were adjusted for age, sex (model 1), BMI, education, smoking, alcohol consumption, habitual physical activity and season of blood sampling (model 2). Spearman and Pearson correlation analyses were performed to obtain correlations coefficients between vitamin D intake, 25-OH D levels, and domain specific cognitive functioning. All analyses were performed using the statistical package SAS, version 9.1 (SAS Institute Inc., Cary, N.C., USA).

Results

Participants of the ProMuscle Study were on average 79 years old and 25-OH D levels decreased with age (P=0.03) see TABLE 1, below. The mean serum 25-OH-D level was 54 nmol/L. However, 17% of the population had 25-OH D3 levels below 30 nmol/L and 53% below 50 nmol/L. Only 23% of the participants showed 25-OH D3 levels ≥75 nmol/L. Mean vitamin D intake was 4.59 μg/d, with 25 percentile of 2.48 μg/d and 75 percentile of 5.78 μg/d. Calcium intake increased across 25-OH D tertiles (P=0.04).

TABLE I

Characteristics of 127 Dutch Frail Elderly per tertile of serum 25(OH)D

|  | T1<br>13-38 nmol/L | T2<br>38-65 nmol/L | T3<br>65-163 nmol/L | P-value |
|---|---|---|---|---|
| N | 40 | 43 | 44 |  |
| Men, n (%) | 16 (40) | 18 (42) | 16 (36) | 0.29 |
| Age | 81.4 ± 7.8 | 78.7 ± 7.8 | 77.0 ± 7.3 | 0.03 |
| Body Mass Index | 27.8 ± 4.4 | 28.0 ± 3.8 | 26.8 ± 4.8 | 0.42 |
| Fasting plasma glucose (mmol/L) | 5.25 ± 0.50 | 5.28 ± 0.44 | 5.24 ± 0.48 | 0.90 |
| Fasting plasma insulin (uU/ml) | 17.35 ± 6.18 | 20.96 ± 7.46 | 16.98 ± 6.67 | 0.01 |
| Homa-IR | 4.1 ± 1.8 | 5.0 ± 2.1 | 4.1 ± 1.9 | 0.04 |
| Chronic disease present, n (%) | 22 (55) | 18 (42) | 26 (59) | 0.25 |
| Systolic Blood Pressure (mmHg) | 152 ± 22 | 144 ± 22 | 144 ± 23 | 0.21 |
| Diastolic Blood Pressure (mmHg) | 75 ± 9 | 75 ± 9 | 74 ± 9 | 0.76 |
| Serum creatinine (mmol/L) | 76.6 ± 15.6 | 74.5 ± 13.1 | 70.9 ± 15.6 | 0.21 |
| Smoking status, n (%) |  |  |  | 0.07 |
| Non-smoker | 35 (88) | 43 (100) | 40 (91) |  |
| Smoker | 5 (12) | 0 (0) | 4 (9) |  |
| Physical activity accelerometer | 91 ± 62 | 136 ± 75 | 184 ± 112 | 0.0001 |
| Educational level, n (%) |  |  |  | 0.26 |
| Primary education | 1 (3) | 3 (7) | 3 (7) |  |
| Secondary education | 28 (70) | 20 (46.5) | 27 (61) |  |
| Higher education | 11 (28) | 20 (46.5) | 14 (32) |  |
| Vitamin D intake (μg/day) | 3.2 (1.7-5.7) | 3.9 (2.5-5.0) | 4.4 (3.0-7.3) | 0.21 |
| Calcium intake (mg/day) | 921 ± 343 | 1029 ± 322 | 1135 ± 476 | 0.04 |
| Alcohol intake (g/day) | 4.5 (0-12.2) | 6.3 (0.1-19.7) | 7.0 (0-20.2) | 0.35 |
| MMSE | 27.5 ± 2.3 | 27.7 ± 2.2 | 27.8 ± 2.2 | 0.81 |
| Attention and working memory | −0.16 ± 0.80 | 0.00 ± 0.86 | 0.14 ± 0.99 | 0.31 |
| Executive functioning | −0.15 ± 0.83 | −0.07 ± 0.74 | 0.25 ± 0.62 | 0.04 |
| Information processing speed | −0.22 ± 0.77 | −0.03 ± 0.87 | 0.24 ± 0.74 | 0.05 |

TABLE I-continued

Characteristics of 127 Dutch Frail Elderly per tertile of serum 25(OH)D

|  | T1<br>13-38 nmol/L | T2<br>38-65 nmol/L | T3<br>65-163 nmol/L | P-value |
|---|---|---|---|---|
| Episodic memory | −0.04 ± 0.76 | −0.11 ± 0.58 | 0.10 ± 0.64 | 0.36 |
| CES-D | 5.55 ± 5.33 | 7.42 ± 4.79 | 7.77 ± 6.77 | 0.17 |

Notes:
values are expressed as a mean ± SD, median with Q1-Q3 or n (%).
Chi-squared tests for categorical variables and 1-way analysis of variance for continuous variables were performed to compare baseline characteristics over tertiles of 25(OH)D.
Chronic disease: defined as kidney disease, liver disease, cardiovascular disease, muscle disease, hip- or knee replacement.
Missing values: physical activity (21), executive function (9), information processing speed (8), fasting plasma insulin, fasting plasma glucose and Homa-IR (3) and blood pressure and creatinine (1).

Vitamin D intake was not significantly correlated with serum 25-OH D3, r=0.09 (P=0.30).

Vitamin D and Cognitive Performance

Compared to participants in the lowest 25-OH D3 tertile, persons in the intermediate and top tertile scored higher on the MMSE, this finding was, however, not significant (see TABLE 2, below). Associations between 25-OH D3 and various cognitive domains are displayed in TABLE 3, below.

TABLE 2

Associations between 25(OH)D and global cognitive performance (MMSE) of 127 elderly participating in the ProMuscle Study

|  | Low<br>0-34 | Moderate<br>34-52 | High<br>52-125 | P for trend |
|---|---|---|---|---|
| Crude model | 1.0 | 0.93 (0.62-1.38) | 0.87 (0.58-1.31) | 0.79 |
| Model 1[a] | 1.0 | 1.00 (0.68-1.47) | 0.98 (0.65-1.47) | 0.96 |
| Model 2[b] | 1.0 | 0.83 (0.55-1.24) | 0.78 (0.51-1.20) | 0.77 |

[a]Adjusted for age and sex.
[b]Adjusted for age, sex, BMI, education (categorical), smoking (categorical), physical activity accelerometer, alcohol intake (categorical) and season
Crude model and model 1: n = 127. Model 2: n = 106.

TABLE III

Associations of 25(OH)D and vitamin D intake with domain-specific cognitive performance in a frail elderly population, β ± SE

|  | Total |  | 'Low' FPG | 'High' FPG |
|---|---|---|---|---|
|  | 25(OH)D | Vitamin D intake[c] | 25(OH)D | 25(OH)D |
| Attention and working memory |||||
| Crude | 0.006 ± 0.003<br>(P = 0.06) | −0.007 ± 0.03<br>(P = 0.78) | 0.004 ± 0.003<br>(P = 0.19) | 0.005 ± 0.005<br>(P = 0.17) |
| Model 1 | 0.005 ± 0.003<br>(P = 0.08) | −0.013 ± 0.03<br>(P = 0.62) | 0.004 ± 0.003<br>(P = 0.26) | 0.007 ± 0.006<br>(P = 0.23) |
| Model 2 | 0.006 ± 0.004<br>(P = 0.11) | −0.02 ± 0.03<br>(P = 0.46) | 0.006 ± 0.004<br>(P = 0.17) | 0.008 ± 0.008<br>(P = 0.31) |
| Executive functioning |||||
| Crude | 0.007 ± 0.002<br>(P = 0.003) | 0.002 ± 0.02<br>(P = 0.94) | 0.007 ± 0.003<br>(P = 0.04) | 0.010 ± 0.004<br>(P = 0.01) |
| Model 1 | 0.006 ± 0.002<br>(P = 0.01) | −0.01 ± 0.02<br>(P = 0.65) | 0.005 ± 0.003<br>(P = 0.11) | 0.009 ± 0.004<br>(P = 0.03) |
| Model 2 | 0.007 ± 0.003<br>(P = 0.01) | −0.05 ± 0.02<br>(P = 0.06) | 0.006 ± 0.004<br>(P = 0.12) | 0.007 ± 0.005<br>(P = 0.17) |
| Information processing speed |||||
| Crude | 0.007 ± 0.003<br>(P = 0.01) | 0.03 ± 0.02<br>(P = 0.24) | 0.007 ± 0.004<br>(P = 0.07) | 0.01 ± 0.004<br>(P = 0.02) |
| Model 1 | 0.006 ± 0.003<br>(P = 0.03) | 0.02 ± 0.02<br>(P = 0.47) | 0.006 ± 0.004<br>(P = 0.14) | 0.008 ± 0.004<br>(P = 0.05) |
| Model 2 | 0.006 ± 0.003<br>(P = 0.06) | 0.01 ± 0.03<br>(P = 0.59) | 0.006 ± 0.004<br>(P = 0.16) | 0.004 ± 0.005<br>(P = 0.42) |
| Episodic memory |||||
| Crude | 0.003 ± 0.002<br>(P = 0.14) | 0.009 ± 0.02<br>(P = 0.65) | 0.003 ± 0.003<br>(P = 0.25) | 0.004 ± 0.004<br>(P = 0.24) |
| Model 1 | 0.002 ± 0.002<br>(P = 0.47) | −0.002 ± 0.02<br>(P = 0.93) | 0.003 ± 0.003<br>(P = 0.49) | 0.002 ± 0.004<br>(P = 0.67) |
| Model 2 | 0.002 ± 0.002<br>(P = 0.28) | −0.03 ± 0.02<br>(P = 0.17) | 0.003 ± 0.003<br>(P = 0.30) | 0.001 ± 0.004<br>(P = 0.74) |

[a]Model 1: Adjusted for age and gender
[b]Model 2: Adjusted for model 1 and BMI, education level, alcohol, smoking, physical activity based upon 7-day accelerometer data and season
[c]Analysis for vitamin D intake are not adjusted for seasonal influence
Crude model and model 1: n = 127 (AWM, EM), n = 118 (EF) and n = 119 (IPS). Model 2: n = 106 (AWM, EM) and n = 99 (EF, IPS).

Fully adjusted models showed significantly better performance in tasks involving executive functioning per 1 nmol/L increase in 25-OH D, g 0.007 (P=0.01). The association between 25-OH D3 and information processing speed almost reached significance, g 0.006 (P=0.06). When the models were expanded to capture the impact of depression or calcium g's did not significantly change (data not shown).

Within the domain executive functioning the association of 25-OH D3 nearly reached significance with the verbal fluency test, showing on average 1 word more recalled with every 17 nmol/L increase in 25-OH D3 (P=0.09). Also a modest association was observed for 25-OH D3 with the Reaction Time Task (neither cued: β−2.86, p=0.01; finger cued: β−2.71, P=0.01; hand cued: β−2.86, P=0.01).

Serum 25-OH D3 showed a significant association with the reaction time task uncued (β−2.58, p=0.01), a task related to the domain information processing speed.

Additionally, a modest association was observed for 25-OH D3 with Digit Span (β0.02, p=0.07), within the domain attention and working memory.

Scores on the Word Learning Tests indicated that with every 11 nmol/L increase in 25-OH D3 one word more could be memorized (P=0.008).

We did not detect any association between vitamin D intake and the various outcome measures. Moreover, correlations between vitamin D intake and 25-OH D3 appeared to be low. In this population we observed a statistical significant association between 25-OH D3 and the domain executive functioning. In this study executive function was assessed using tasks related to response inhibition, cognitive flexibility and mental shifting.

EXAMPLE 2

The Effect of 25(OH) Vitamin D3 on Executive Function

A Double-Blind, Randomized, Placebo-Controlled Trial in the Frail Elderly

Primary and Secondary Objectives

The primary objective of the study is to assess the effect of 25-OH D3 in comparison to Vitamin D3 on executive function in frail elderly with a low Vitamin D status. The secondary objective is to assess 25-OH D3 effect on increasing 25-OH D3 serum level in comparison to Vitamin D3.

Study Design, Participants and Treatment

The design is a parallel group, randomized, placebo-controlled, double-blind study with three different application groups. Each group has an appropriate number of participants (e.g., 20 participants). Eligibility is defined as being 65 years or older and being frail or pre-frail. Frailty is defined as having unintentional weight loss, weakness, self-reported exhaustion, slow walking speed, and/or low physical activity (see Fried L P, et al. Frailty in older adults: evidence for a phenotype. *J Gerontol A Biol Sci Med Sci.* March 2001; 56(3):M146-156.)

A participant is classified as pre-frail when one or two of the aforementioned criteria are met, while frail is classified when three or more criteria are present. The study subjects have to have a plasma 25-OH D3 levels below 50 μmol/L. The treatment conditions are either 25-OH D3, Vitamin D3 (dry Vitamin D3 100 SD/S), the combination of 25-OH D3 and Vitamin D3, or placebo. The duration of supplementation is 6 months (180 days).

Study Procedures

Participants are randomly allocated to either the 25-OH D3 group (N=20), Vitamin D3 group (N=20), Vitamin D3+25-OH D3 group (N=20) or placebo group (N=20). Double-blind randomization is carried out by means of a label code associated with a specific participant ID number, whose meaning is known only to the supplier. Participants are allocated randomly to these numbers.

At screening (in between Day −14 to Day 0) the following tests are performed to screen for serum 25-OH D3 levels below 50 μmol/L:Serum:25-OH D3, Vitamin D3, calcium, creatinine, albumin; urine: calcium and creatinine; blood pressure.

For baseline (Day 0) the following tests are performed: Physical examination, vital signs (blood pressure, heart rate), demographics, clinical laboratory, FFQ, serum: 25-OH D3, 24,25-OH 2D, 1,25(OH)2D3, Vitamin D3, calcium, albumin, creatinine, fasting glucose, PTH; urine: calcium, creatinine; executive function tests (see below). Baseline evaluation is followed by the randomization of the subjects. From Day 2 on, they start to take the study compounds. Daily dosages for those receiving 25-OH D3 are 5-25 μg per day or 35-175 μg per week. For Vitamin D3, dosages range from 5-25 μg per day, or 35-175 μg per week. For the combination administration, the same ranges of both actives are administered.

At visits on Day 90 and Day 180 the following tests are performed: Vital signs (blood pressure, heart rate), serum: calcium, creatinine, albumin, 25-OH D3, 24,25(OH)2D, 1,25(OH)2D3, VD3, fasting glucose; urine: calcium and creatinine; compliance; executive function tests. In addition, at visit on Day 180 the following tests are performed: Physical examination, clinical laboratory, serum PTH, urine DPD.

Executive functioning test batteries include the following standard tests of executive functioning: Trail Making Tests A and B (to determine the ratio of TMT-B/TMT-A), Stroop Colour-Word Test, including determining the Stroop ratio, calculated by Stroop card 3/((Stroop card 1+Stroop card 2)/2) and animal fluency test. These tests are always performed at the same time of the day.

Results

25-OH D3 has a significantly higher effect on the improvement of executive functioning in frail elderly in comparison to Vitamin D3 and placebo, respectively. Also, the group receiving 25 OH D3+Vitamin D3 is seen to have a higher sustained plasma 25-OH D3 level than groups receiving either active alone; and thus use of this combination in a weekly dose is also effective.

Furthermore, it is being shown that administration of 25-OH D3 significantly increases 25-OH D3 serum level in comparison to administration of only Vitamin D3.

EXAMPLE 3

The Effect of 25(OH) Vitamin D3 on Executive Function

A Double-Blind, Randomized, Placebo-Controlled Trial in the General Adult Population Study Design, Participants and Treatment The design is a parallel group, randomized, placebo-controlled, double-blind study similar to that of Example 2, above, except that the participants are healthy adults under 65. The duration of supplementation is 6 months (180 days). Group size is chosen so that a statistically significant difference, if present, may be observed between placebo and test groups.

Study Procedures

Participants are randomly allocated to either the 25-OH D3 group, Vitamin D3 group, (Vitamin D3+25-OH D3) group or placebo group. Double-blind randomization is carried out by means of a label code associated with a specific participant ID number, whose meaning is known only to the supplier. Participants are allocated randomly to these numbers.

For baseline (Day 0) the following tests are performed: Physical examination, vital signs (blood pressure, heart rate), demographics, clinical laboratory, FFQ, serum: 25-OH D3, 24,25(OH)2D, 1,25(OH)2D3, Vitamin D3, calcium, albumin, creatinine, fasting glucose, PTH; urine: calcium, creatinine; executive function tests (see below). Baseline evaluation is followed by the randomization of the subjects. From Day 2 on, they start to take the study compounds.

At visits on Day 90 and Day 180 the following tests are performed: Vital signs (blood pressure, heart rate), serum: calcium, creatinine, albumin, 25-OH D3, 24,25(OH)2D, 1,25(OH)2D3, VD3, fasting glucose; urine: calcium and creatinine; compliance; executive function tests. In addition, at visit on Day 180 the following tests are performed: Physical examination, clinical laboratory, serum PTH, urine DPD.

Executive functioning test batteries include the following standard tests of executive functioning: Trail Making Tests A and B (to determine the ratio of TMT-B/TMT-A), Stroop Colour-Word Test, including determining the Stroop ratio, calculated by Stroop card 3/((Stroop card 1+Stroop card 2)/2) and animal fluency test. These tests are always performed at the same time of the day.

Results

Positive results are seen in comparison to placebo. The group receiving a weekly dose of the combination is also significantly different from placebo.

Furthermore, it is being shown that administration of 25-OH D3 significantly increases 25-OH D serum level in comparison to administration of only Vitamin D3.

What is claimed is:

1. A method of enhancing, maintaining, or lessening decrease of a cognitive executive function performance comprising:
administering to a healthy human desirous of enhancing or maintaining executive functioning or desirous of lessening the decrease of cognitive-executive-function an effective amount of 25-OH D3.

2. The method according to claim 1, wherein the method comprises administering orally the 25-OH D3.

3. The method according to claim 1, wherein the method comprises administering the 25-OH D3 in combination with Vitamin D.

4. A kit for enhancing or maintaining executive function or for lessening a decrease in executive function comprising:
a) at least one dosage form of 25-OH D3; and
b) information which informs a prospective user about the benefits of using 25-OH D3 in enhancing or maintaining executive function, or lessening a decrease in executive function in healthy individuals.

5. The kit according to claim 4, wherein the kit further comprises vitamin D.

* * * * *